(12) United States Patent
Blaschke

(10) Patent No.: US 7,182,839 B2
(45) Date of Patent: Feb. 27, 2007

(54) PREVENTING DEPOSITION OF FOULING AGENTS ONTO EQUIPMENT

(75) Inventor: Marilyn Wood Blaschke, Richmond, TX (US)

(73) Assignee: Baker Hughes Incorporated, Houston, TX (US)

( * ) Notice: Subject to any disclaimer, the term of this patent is extended or adjusted under 35 U.S.C. 154(b) by 669 days.

(21) Appl. No.: 09/923,042

(22) Filed: Aug. 6, 2001

(65) Prior Publication Data

US 2003/0049161 A1    Mar. 13, 2003

(51) Int. Cl.
*B01D 3/34* (2006.01)
*C07C 7/20* (2006.01)
*C23F 14/00* (2006.01)

(52) U.S. Cl. .................. 203/6; 203/7; 203/51; 203/57; 585/4; 585/860; 585/864; 208/48 AA; 422/16; 422/17

(58) Field of Classification Search ............. 203/6, 203/7, 51, 57, 60, 67, 62–65, 69–70; 585/4, 585/833, 864–867, 860; 208/48 AA, 47; 210/698; 422/16, 17
See application file for complete search history.

(56) References Cited

U.S. PATENT DOCUMENTS

| | | | |
|---|---|---|---|
| 3,666,656 A * | 5/1972 | Stanley ................. | 208/48 AA |
| 4,268,403 A | 5/1981 | Buchman et al. | |
| 4,410,419 A | 10/1983 | Ferm | |
| 4,902,824 A * | 2/1990 | Syrinek ................. | 560/248 |
| 5,243,063 A * | 9/1993 | Devicaris et al. ........... | 558/304 |
| 5,388,644 A | 2/1995 | Romocki | |
| 5,650,072 A * | 7/1997 | Mc Clain et al. ........... | 210/698 |
| 5,746,924 A * | 5/1998 | Cooper et al. .............. | 210/698 |
| 5,756,606 A * | 5/1998 | Wong ........................ | 526/94 |
| 6,030,971 A | 2/2000 | Whittemore et al. | |
| 6,040,489 A | 3/2000 | Imai | |

FOREIGN PATENT DOCUMENTS

ZA    68/05343    8/1968

OTHER PUBLICATIONS

Hollis et al, "control of scale on aqueous systems". S. African ZA 6805343, 196901123, 13. pp.(72:35664).*
Goko et al "Manufacture of propylene polymers in gas phase reactors using fouling inhibitors" Jpn. Kokai Tokkyo koho JP 01045407 A2 19890217 Heisei, 6 pp. (111:58515).*
Kawase, Yasuhito; Technical series Distillation: Extractive distillation; Kaguku Kogaki (2001), 65(2), 91-93.
Van Dyk, Braam; Nieuwoudt, Izak; Design of Solvents of Extractive Distillation; Ind. Eng. Chem. Res. (2000), 39(5), 1423-1429.
Kim, K.J. Diwekar, U.M.; Joback, K.G.; Solvent selection under uncertainty; Abstr. Pap.—Am. Chem. Soc. (2000), 220th, IEC-090.
S.A.H. Zaidi; Sutdy fo Salt Effects on the Extractive Distillation of 1- and 2-Propanol-Benzene Systems; J. Gen Chem. USSR (Engl. Transl.) 1987, 57 : 3 600.
I.M. Marchenko, et al., Features of Extractive Distillation in the Presence of Low-Boiling Zeotropic Agents; J. Appl. Chem. USSR (Engl. Transl.) 1992, 65 : 3.2 500.
Andrew W. Sloley, Petroleum Refining; http://www.asloley.home.mindspring.com/ref00001.html; 1998.
TR-447 Toxicology and Carcinogenesis Studies of Acetronitrile (CAS No. 75-05-8) in F344/N Rats and B6C3F$_1$ Mice (Inhalation Studies); Apr. 1996.
Sulfolane Process; http://www.uop.com/home/petrochemcials/processes_products/sulfolane_intro.htm.
Benzene Technical Data Sheet; Bayer AG, GB-CH; http://www.erdoelchemie.de/englisch/products/benzene.html.
Goko, et al.; Manufacturing Method of Propylene Polymers: JPO Official Gazette of Unexamined Patent Applications; Feb. 17, 1989; pp. 45-50; Jap. Pat. Appl. Publ. No. 64-45407.

* cited by examiner

*Primary Examiner*—Virginia Manoharan
(74) *Attorney, Agent, or Firm*—Paula D. Morris; Morris & Amatong, P.C.

(57) ABSTRACT

Methods and compositions effective to prevent deposition of fouling agents, preferably polymerization precursors, on handling equipment, particularly during solvent recovery.

37 Claims, No Drawings

PREVENTING DEPOSITION OF FOULING AGENTS ONTO EQUIPMENT

FIELD OF INVENTION

The present invention relates to methods and compositions to prevent deposition of fouling agents onto handling equipment. Specifically, the invention relates to the use of N,N-disubstituted amides, most preferably N,N-dialkylamides, in solvent recovery systems to prevent deposition of solids formed prior to or during solvent recovery in a diene plant.

BACKGROUND OF INVENTION

A frequent problem in the chemical industry is deposition of insoluble materials onto equipment handling reactant and product streams. One area where this problem is manifested is in solvent recovery units. Fouling of reboilers and trays of distillation columns occurs due to precipitation of fouling agents. Fouling or deposition during solvent recovery causes flow and temperature control problems, both of which reduce the efficiency of the solvent recovery process and increase maintenance costs of the unit.

Sometimes fouling can be partially ameliorated by adding a polymerization inhibitor to inhibit polymerization of unsaturated moieties, such as 1,3-butadiene or isoprene. However, polymerization inhibitors usually do not stop all of the polymerization, and therefore do not stop all of the fouling by these agents. Plus, the feed to a solvent distillation column may already contain polymer which precipitates and fouls the heat exchangers and trays of the distillation tower.

Methods of treating streams are needed which effectively prevent or resolve fouling of the equipment used to handle fouling agents.

SUMMARY OF THE INVENTION

The present invention provides a method for preventing fouling of equipment handling one or more fouling agents comprising treating a blend comprising said one or more fouling agents with an N,N-disubstituted amide in an amount and under conditions effective to form a dispersion of said one or more fouling agents in said blend and to prevent said one or more fouling agents from depositing on said equipment under conditions of operation of said equipment.

DETAILED DESCRIPTION OF THE INVENTION

The present invention provides a method to prevent or minimize fouling of "equipment handling one or more fouling agents." As used herein, the phrase "equipment handling one or more fouling agents" is defined to mean equipment other than downhole equipment designed to drill for and/or remove crude oil from a geological formation. The phrase "equipment handling one or more fouling agents" refers to industrial equipment for processing bulk streams comprising fouling agents. Such equipment includes, but is not necessarily limited to, equipment for handling: refinery streams; petrochemical streams; streams comprising alkenes; streams comprising conjugated dienes; streams comprising alkynes; streams comprising di-isocyanates; streams comprising carboxylic acids; streams comprising di-carboxylic acids; streams comprising acid chlorides; streams comprising di-acid chlorides; and, streams comprising diols, among others.

The invention prevents or minimizes fouling by deposition from a "blend" defined as a stream comprising one or more fouling agents, for example, onto components of "equipment handling one or more fouling agent, preferably, on components of a solvent recovery system. Such components include, but are not necessarily limited to heat exchangers, the bottom of the distillation column, reboilers, transfer lines, pumps, and any other components in which "fouling agents" are handled or transported.

As used herein, the term "fouling agents" is defined as polymers, prepolymers and/or other materials which would become insoluble in and/or precipitate from a stream or "blend" and foul the equipment under the conditions of operation of the equipment, of which a preferred embodiment is a solvent recovery system. The invention involves treating the stream or "blend," that is fed to equipment handling one or more fouling agents, preferably to a blend that is fed to a solvent recovery system, with an additive comprising a dispersant, preferably an N,N-disubstituted amide.

Without limiting the invention to a particular mechanism of action (unless specified in a claim), the dispersant, preferably an N,N-disubstituted amide, is believed to disperse the fouling agent(s) in the "blend," thereby preventing agglomeration and deposition of fouling agents. Maintaining the solid or semi-solid fouling agents in a "dispersion" in the remainder of the blend renders the fouling agents unable to precipitate onto the solvent recovery equipment.

The blend fed to the unit comprises a solvent. The solvent may be substantially any organic solvent. Various solvents are used depending, for example, upon the type of solvent recovery unit treated and the product being made or processed. In a preferred embodiment, the solvent is an "extractive distillation solvent." As used herein, the term "extractive distillation" refers to distillation that uses a solvent to increase the difference between (a) the volatility or boiling point of undesired components that would be inseparable by conventional distillation procedures from a substance or substances to be extracted and (b) a substance or substances to be extracted.

Solvents used in extractive distillation processes typically are thermally stable and non-corrosive. Extractive distillation solvents typically are polar solvents, and include, but are not necessarily limited to halogenated aromatics, alcohols, cyclic and acyclic amides, cyclic and acyclic organo-carbonates, sulfones, glycols, polyglycols, phenols, amines, nitrites, and aldehydes. Specific examples of such solvents include, but are not necessarily limited to, acetonitrile, beta-methoxypropionitrile, di- and tri-chlorobenzene, benzyl alcohol, N-methylpyrrolidinone (NMP), N,N-dimethylformamide (DMF), N,N-dimethylacetamide (DMAc), propylene carbonate, 2-furaldehyde and SULFOLANE®.

Recovery of an extractive distillation solvent preferably is by "distillation" performed after the desired product of the extractive distillation process has been recovered. It is desirable to recover the extractive distillation solvent from the remaining "blend." The "fouling agents" in the remaining blend may have a boiling point that is lower than or higher than the extractive distillation solvent. According to the present invention, the blend is distilled at temperatures that free the extractive distillation solvent from both lower and higher boiling contaminants, including, but not necessarily limited to water (by azeotropic distillation with solvent), 1,3-butadiene, 1-butene, 2-butene, butane, acetylene, methylacetylene, dimethylacetylene, allene, 1,2-butadiene and fouling agents.

The blend is treated with an N,N-disubstituted amide, which acts as a "dispersant" for fouling agents in the blend. Examples of N,N-disubstituted amides suitable for use in the invention have the following general structure:

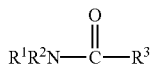

wherein
  $R^1$ and $R^2$ independently are selected from the group consisting of hydrogen atoms; hydroxyalkyl groups having from about 1 to about 3 carbon atoms; aryl groups; aralkyl groups; alkaryl groups; branched or unbranched alkyl groups (and alkenyl groups) having from about 1 to about 30 carbon atoms, preferably from about 1 to 6 carbon atoms, most preferably from about 1 to 4 carbon atoms; cyclic groups having a total number of from about 4 to about 6 carbon atoms; and, cyclic groups wherein $R^1$ and $R^2$ are connected either directly or via a heteroatom to form a cyclic group having a total number of members of from about 5 to about 7, wherein said heteroatom is selected from the group consisting of nitrogen, oxygen, and sulfur;
  $R^3$ is selected from the group consisting of hydrogen, aryl groups, alkaryl groups, aralkyl groups and branched or unbranched alkyl groups (or alkenyl groups) having from about 1 to 30 carbon atoms, more preferably, from about 12 to 30 carbon atoms, most preferably from about 16 to 22 carbon atoms.

When $R^1$ and $R^2$ are connected to form a cyclic amide, and said cyclic amide comprises a nitrogen heteroatom, $R^1$ and $R^2$ each contain 2 carbon atoms and said nitrogen heteroatom comprises a substituent selected from the group consisting of hydrogen, a hydroxyalkyl group having from about 1 to about 3 carbon atoms, and an alkyl group having from about 1 to about 6 carbon atoms, preferably from about 1 to about 3 carbon atoms.

When $R^1$ and $R^2$ are branched or unbranched alkenyl, or independently are a hydrogen atom and alkenyl, $$R^1 \text{ or } R^2 = CF_n H_{2n-z}$$

and;
  when n is an even number, $R^1$ or $R^2$ comprises a quantity of carbon-carbon double bonds and said quantity increases from 1 to 2 to 3, to 4 to a maximum of n/2, with z following a first progression 1, 3, 5, 7, . . . to n−1, depending of the number of alkene groups present; and
  when n is an odd number and said quantity increases from 1 to 2 to 3, to 4 to a maximum of (n−1)/2, with z following a second progression, 1, 3, 5, 7, . . . to n−2.

In a preferred embodiment,
  $R^1$ and $R^2$ independently are selected from the group consisting of hydrogen atoms; hydroxyalkyl groups having from about 1 to about 3 carbon atoms; branched or unbranched alkyl groups and alkenyl groups having from about 1 to about 30 carbon atoms, preferably from about 1 to 6 carbon atoms, most preferably from about 1 to 4 carbon atoms; and,
  $R^3$ is selected from the group consisting of hydrogen, aryl groups, aralkyl groups, alkaryl groups and branched or unbranched alkyl groups (and alkenyl groups) having from about 1 to 30 carbon atoms, more preferably, from about 12 to 30 carbon atoms, most preferably, from about 16 to 22 carbon atoms.

Preferred embodiments of the dispersant will vary depending upon the system being treated. In a preferred embodiment for treating a butadiene solvent recovery system:
  $R^1$ and $R^2$ preferably are selected from the group consisting of hydrogen, methyl, ethyl, propyl, iso-propyl and butyl groups; and,
  $R^3$ is selected from the group consisting of alkyl groups, alkenyl groups, and combinations thereof having from about 16 to about 22 carbon atoms.

In a preferred embodiment, the N,N-disubstituted amide is an amide of a fatty acid. The fatty acid residue may be a substituted or unsubstituted residue of a fatty acid which occurs in a vegetable oil. Suitable vegetable oils include, but are not necessarily limited to tall oil, palm oil, soybean oil, cottonseed oil, coconut oil, corn oil, peanut oil, canola oil, safflower oil, sunflower oil, babassu oil, castor oil, linseed oil, olive oil, and tung oil. In a preferred embodiment, the vegetable oil is selected from tall oil, palm oil, and soybean oil. Preferred fatty acids have from about 6 to about 22 carbon atoms, more preferably about 8 to about 22 carbon atoms.

A most preferred N,N-disubstituted amide used to minimize fouling in a 1,3-butadiene units is an N,N-disubstituted amide of a tall oil fatty acid, most preferably the N,N-dimethyl amide of tall oil (DMATO). The amide of the vegetable oil, as defined above, is prepared by reacting the vegetable oil with an appropriate amine. For example, the dimethylamide of tall oil (DMATO) is prepared by reacting the tall oil fatty acids (TOFA) with dimethylamine.

Tall oil is a natural product isolated from pine trees by means of the Kraft pulping process. Components of tall oil include, but are not necessarily limited to: rosin acids, fatty acids and unsaponiflables. Tall oil is refined by distillation. Several grades of TOFA are available depending on rosin content, unsaponifiables content, color and color stability. TOFA which have been sold in the United States, typically have the following composition (Ref.—Ullmann's Encyclopedia of Industrial Chemistry, 1985, Editors—Elvers et al., Fifth edition, Vol. A 26, pg. 67):

| Properties and Composition | | Value |
|---|---|---|
| Acid number | | 197 |
| Rosin acids, | | 1% |
| Unsaponifiables, | | 1.5% |
| Iodine value | | 130 |
| Color, Gardner | | 3 |
| Fatty acids, % | | |
| Saturated | | 2% |
| Oleic | (18:1) | 48% |
| Linoleic | (18:2) | 37% |
| Linolenic | (18:3) | 3% |
| Conjugated | (18:2) | 6% |
| Other | | 2.5% |

The N,N-disubstituted amide may be made in any suitable manner known to persons of ordinary skill in the art. An example is described in Furniss et al., Vogel's Textbook of Practical Organic Chemistry, 1989, 5$^{th}$ Edition, pg. 708, incorporated herein by reference. Preferred N,N-dialkylamides are made as described in U.S. Pat. No. 4,388,644, incorporated herein by reference.

Basically, the fatty acid and the appropriate amine are combined under elevated temperature and pressure. In the case of DMATO, for example, the TOFA fraction (1.0 mole) is mixed with a slight molar excess (1.1 mole) of dimethylamine. In the cases of other vegetable oils (soybean, palm) in which the fatty acids are present as triglycerides (3 fatty acids/triglyceride), 1.0 mole of the oil is mixed with 3.3 moles of the dimethylamine. These mixtures are heated slowly in a closed vessel to 170° C. at a pressure not to exceed 100 p.s.i. The reaction is held at this point for eight hours. The process has been shown to achieve at least 95 percent amidation of the constituent fatty acids. In the case of DMATO, excess amine is removed in the aqueous phase formed by the water produced in the reaction. Where triglycerides are involved, excess amine is present in the glycerol phase removed after the reaction.

Although it is not nececessary for the N,N-dialkylamide to contain any solvent or additives, formulations of N,N-dialkylamides that do contain common additives such as surfactants, emulsifiers or dispersants can also be used in the methods of this invention. A preferred formulation of a N,N-dialkylamide is "DMAD," which is commercially available from Buckman Laboratories of Canada, Ltd., Vaudreuil, Quebec, Canada.

In a preferred embodiment, the dispersant comprises water and a relatively polar cosolvent that is compatible with the blend being treated and that is effective to liquefy the active component, preferably an N,N-disubstituted amide. Suitable relatively polar cosolvents include, but are not necessarily limited to acetonitrile, benzene, toluene, xylenes, heavy aromatic naphtha, kerosene, mono-butyl ether of diethylene glycol, and combinations thereof. If additives and/or solvents or cosolvents are used, the minimum amount of dispersant in the additive for a given system will depend upon the quantity of the fouling agent in the stream to be treated. A minimum amount still must be effective to form a dispersion of the fouling agents in the blend and to prevent the fouling agents from depositing on said equipment under conditions of operation of said equipment. The additive may comprise up to 100% N,N-dimethylamide of a tall oil fatty acid. A most preferred embodiment is 10% N,N-dimethyl amide, 40% butyl carbitol, and 50% water.

For ease in handling, the dispersant preferably is added in liquid form, with or without a liquifying solvent, using a metering pump. The optimum amount of dispersant for use with a particular system will be readily determined by persons of ordinary skill in the art using a simple test. An exemplary test is the following:

To a 500 mL flask equipped with distillation column, thermocouple, a spin bar and metal coupon is added 250 mL of the blend to be treated and a known dose of additive (e.g., 10 ppm of dispersant). The coupon is adjusted so that half of the coupon is inmmersed into the liquid phase. The flask is then heated to reflux. Distillation ensues and distillate is collected until visible precipitation is observed. Then distillation is continued until a significant additional amount of solids are observed. The percentage of solvent or solvents distilled is recorded and the flask contents are cooled to room temperature. The remaining liquid in the reaction flask is carefully removed and any material that adheres to the coupon, thermocouple, spin bar and the internals of the flask is dissolved in acetone/IPA. This solution is transferred to a beaker, dried, and weighed. The time required is 1.5 hours for distillation, 15 minutes for dissolving residue and 15 minutes for drying.

The test is repeated with higher dosages of additive; e.g., 20, 50, 100 and 200 ppm. Each sample is distilled until the volume % distillate is the same as in the first (10 ppm of dispersant) sample tested. If the optimum (minimum) residue (fouling) occurs at a dose between, 10 and 200 ppm, the evaluation is complete. If 200 ppm of additive produces the least fouling, the test is repeated at higher doses until an optimum dose is found.

Where the solvent recovery system is a part of an extractive distillation process, wherein the solvent to be recovered is acetonitrile, the procedure would be:

To a 500 mL flask equipped with fractional distillation column, thermocouple, a spin bar and metal coupon is added 250 mL of SRC (solvent recovery column) feed and a known dose of additive (e.g., 10 ppm of dispersant). The coupon is adjusted so that half of the coupon is immersed into the liquid phase. The flask is then heated to 213° F. Distillation ensues and the overhead material is collected in aliquots, noting carefully the amount, temperature, pH and appearance. After the pH of the overhead samples drops to below a pH of 8, the flask contents are cooled to room temperature. The remaining liquid in the reaction flask is carefully removed and any material that adheres to the coupon, thermocouple, spin bar and the internals of the flask is dissolved in acetone/IPA. This solution is transferred to a beaker, dried, and weighed. The time required is 1.5 hours for distillation, 15 minutes for dissolving residue and 15 minutes for drying.

The test is repeated with higher dosages of additive; e.g., 20, 50, 100 and 200 ppm. If the optimum (minimum) residue (fouling) occurs at a dose between, 10 and 200 ppm, the evaluation is complete. If 200 ppm of additive produces the least fouling, the test is repeated at higher doses until an optimum dose is found.

An effective amount of the dispersant is an amount effective to prevent the deposition of at least about 60% of the deposits that form in the absence of the dispersant, more preferably at least about 75%, even more preferably at least about 80%., and most preferably at least about 90% of the deposits. Typically this will require from about 1 ppm to about 1,000 ppm of the dispersant, preferably as small an amount as possible, most preferably from about 10 to about 100 ppm. Where the dispersant is an N,N-dimethyl amide and the blend is the feed to the solvent recovery column of a 1,3-butadiene unit, from about 20 ppm to about 50 ppm of the N,N-disubstituted amide is an effective amount.

The dispersant is added to the "blend" at any acceptable point in a given process. Where the "blend" does not include a solvent recovery tower feed, the dispersant may simply be added to the separation component or reactor used to handle the blend. Where the blend does comprise a solvent recovery tower, the dispersant preferably is added to the solvent recovery tower feed line before it enters the tower.

A solvent commonly used for extractive distillation of 1,3-butadiene is acetonitrile. The addition of the dispersant, preferably the N,N-dimethylamide of tall oil fatty acids, prevents oligomers, polymers, 1,3-butadiene and other unsaturated moieties remaining in the blend from fouling the equipment during the distillation process to recover the acetonitrile.

Where the dispersant is used to recover acetonitrile present in a blend after extractive distillation and recovery of the 1,3-butadiene product, the dispersant may be added at a variety of points. In a preferred embodiment, the dispersant is added to the feed to the solvent recovery column of a 1,3-butadiene unit. The solvent is recovered by fractional distillation to free it from both higher and lower boiling contaminants. Such contaminants include, but are not limited to, 1,3-butadiene, methylacetylene, dimethylacetylene, allene, 1,2-butadiene, oligomers and polymers.

The invention will be better understood with reference to the following example, which is illustrative only:

EXAMPLE I

A test method was developed to simulate the fouling in a solvent recovery column of a 1,3-butadiene plant. The test consisted of heating a sample of SRC (Solvent Recovery Column) feed to 213° F. containing an amount of antifoulant, then distilling liquid overhead until the pH of the overhead liquid dropped to 8, cooling the flask contents, decanting the liquid, dissolving the residue formed in a blend of acetone and 2-propanol, evaporating the solvents and weighing the polymeric residue. Five samples and a blank were run.

In the procedure, N,N-dimethyl amide of tall oil fatty acids DMAD was obtained from Buckman Chemical Company, Memphis, Tenn. The performance of DMAD was compared to the performance of imidazoline, a commercially available anti-fouling product.

To a 500 mL flask equipped with fractional distillation column, thermocouple, a spin bar and metal coupon was added 250 mL of SRC feed and a known dose of dispersant. The coupon was adjusted so that half of the coupon was immersed into the liquid phase. The flask contents were then heated to 213° F. Distillation ensued and the overhead material was collected in aliquots, noting carefully the amount, temperature, pH and appearance. After the pH of the overhead samples dropped to below a pH of 8, the test was concluded. After cooling to room temperature, the remaining liquid in the reaction flask was carefully removed and any material that was adhered to the coupon, thermocouple, the spin bar and the internals of the flask was dissolved in acetone/IPA. This solution was transferred to a beaker, dried, and weighed. The time required for each step is 1.5 hours for distillation, 15 minutes for dissolution of residue and 15 minutes for solvent evaporation.

The amount of residue that was measured included both existent polymeric products and those that were formed during the test. Products were evaluated on the ability to inhibit the deposition of polymeric materials. The results are given in the following Table (each "Sample Date" represents a different sample of SRC feed):

| PRODUCT | SAMPLE DATE | ppm | % INHIBITION |
|---|---|---|---|
| BLANK | — | | 0 |
| An imidazoline dispersant | Oct. 24, 2000 | 50 | 90 |
| N,N-dimethyl amide of tall oil fatty acids | Oct. 24, 2000 | 50 | 100 |
| N,N-dimethyl amide of tall oil fatty acids | Nov. 16, 2000 | 250 | 100 |
| N,N-dimethyl amide of tall oil fatty acids | Nov. 16, 2000 | 50 | 100 |
| N,N-dimethyl amide of tall oil fatty acids | Dec. 07, 2000 | 50 | 100 |

As can be seen from the above Table, the N,N-dimethyl amide of tall oil fatty acids completely inhibited fouling under the conditions of this test. The test demonstrates the ability of an N,N-dimethyl fatty amide to perform over a long time frame and varying conditions of the feed stream. This ability to inhibit the deposition may result from the capacity of the product to disperse the polymeric material into the stream and/or from the capacity of the product to limit the polymerization of reactants in the stream.

The minimum dosage for purposes of the test had been determined to be around 50 ppm. The possibility of a lower dosage was not explored in this set of tests. It is important to note that no foaming was observed in this test with any of the additives and the test stream.

Many modifications may be made to the present invention without departing from the spirit and scope of the present invention. The embodiment described herein is meant to be illustrative only and should not be taken as limiting the invention, which is defined in the following claims.

I claim:

1. A method for preventing fouling of equipment during solvent recovery in a diene plant producing a compound selected from the group consisting of 1,3-butadiene and isoprene, the method comprising treating a solvent recovery blend comprising extractive distillation solvent and at least one fouling agent with N,N-dialkyl amide of fatty acid in an amount of at least 20 ppm.

2. The method of claim 1 wherein said amount is least 50 ppm.

3. The method of claim 1 further comprising separating said solvent from said blend.

4. A method for inhibiting fouling of equipment during solvent recovery in a diene plant producing a compound selected from the group consisting of 1,3-butadiene and isoprene, the method comprising treating a solvent recovery blend comprising extractive distillation solvent and at least one fouling agent with an N,N-dialkyl amide of tall oil fatty acid in an amount of at least 20 ppm.

5. The method of claim 4 wherein said amount is least 50 ppm.

6. A method for inhibiting fouling of equipment during solvent recovery in a diene plant producing a compound selected from the group consisting of 1,3-butadiene and isoprene, the method comprising treating a solvent recovery blend comprising extractive distillation solvent and at least one fouling agent with N,N-dimethyl amide of fatty acid in an amount at least 20 ppm.

7. The method of claim 6 wherein said amount at least 50 ppm.

8. The method of claim 7 wherein said fatty acid is tall oil fatty acid.

9. The method of claim 6 wherein said fatty acid is tall oil fatty acid.

10. A method for inhibiting fouling of equipment during solvent recovery in a diene plant producing a compound selected from the group consisting of 1,3-butadiene and isoprene, the method comprising treating a solvent recovery blend comprising extractive distillation solvent and at least one fouling agent with N,N-disubstituted amide in an amount and under conditions effective to inhibit said fouling.

11. The method of claim 10 further comprising separating solvent from said blend.

12. The method of claim 11 wherein said N,N-disubstituted amide is an N,N-dialkyl amide comprising alkyl groups having from about 16 to about 22 carbon atoms.

13. The method of claim 11 wherein said N,N-disubstituted amide is amide of fatty acid.

14. The method of claim 10 wherein said N,N-disubstituted amide is an N,N-dialkyl amide comprising alkyl groups having from about 16 to about 22 carbon atoms.

15. The method of claim 14 wherein said N,N-disubstituted amide is amide of fatty acid.

16. The method of claim 10 wherein said N,N-disubstituted amide is amide of tall oil fatty acid.

17. A method for inhibiting fouling of equipment during solvent recovery in a diene plant producing a compound selected from the group consisting of 1,3-butadiene and isoprene, the method comprising:
treating a solvent recovery blend comprising extractive distillation solvent and at least one fouling agent with dispersant in an amount and under conditions effective to inhibit said fouling, and,
providing as said dispersant N,N-disubstituted amide having the following general formula:

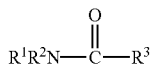

wherein:
$R^1$ and $R^2$ independently are selected from the group consisting of hydrogen atoms; hydroxyalkyl groups having from about 1 to about 3 carbon atoms; aryl groups, aralkyl groups, alkaryl groups, branched or unbranched alkyl groups and alkenyl groups having from about 1 to about 30 carbon atoms; cyclic groups having a total number of from about 4 to about 6 carbon atoms; and, cyclic groups wherein $R_1$ and $R_2$ are connected either directly or via a heteroatom to form a cyclic group having a total number of members of from about 5 to about 7, wherein said heteroatom is selected from the group consisting of nitrogen, oxygen, and sulfur;
$R_3$ is selected from the group consisting of hydrogen, aryl groups, alkaryl groups, aralkyl groups, and branched or unbranched alkyl and alkenyl groups having from about 1 to 30 carbon atoms.

18. The method of claim 17 further comprising separating solvent from said blend.

19. The method of claim 17:
provided that,
when $R^1$ and $R^2$ are connected to form a cyclic amide, and said cyclic amide comprises a nitrogen heteroatom, $R^1$ and $R^2$ each contain 2 carbon atoms and said nitrogen heteroatom comprises a substituent selected from the group consisting of hydrogen, a hydroxyalkyl group having from about 1 to about 3 carbon atoms, and an alkyl group having from about 1 to about 6 carbon atoms; and,
provided that when $R^1$ is selected from the group consisting of a hydrogen atom and alkenyl group, $R^2$ is $C_nH_{2n-z}$ wherein, when n is an even number, $R^1$ or $R^2$ has a quantity of carbon-carbon double bonds and said quantity increases from 1 to 2 to 3, to 4 to a maximum of n/2, with z following a first progression 1, 3, 5, 7, to n−1, depending of the number of alkene groups present; and when n is an odd number and said quantity increases from 1 to 2 to 3, to 4 to a maximum of (n−1)/2, with z following a second progression, 1, 3, 5, 7, . . . to n−2.

20. The method of claim 19 wherein $R_3$ is selected from the group consisting of branched and unbranched alkyl and alkenyl groups having from about 16 to 22 carbon atoms.

21. The method of claim 17 wherein $R^3$ is selected from the group consisting of branched and unbranched alkyl and alkenyl groups having from about 16 to 22 carbon atoms.

22. A method for inhibiting fouling of equipment during solvent recovery in a diene plant producing a compound selected from the group consisting of 1,3-butadiene and isoprene, the method comprising:
treating a solvent recovery blend comprising extractive distillation solvent and at least one fouling agent with dispersant in an amount and under conditions effective to inhibit said fouling; and,
providing as said dispersant N,N-disubstituted amide having the following general formula:

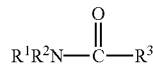

wherein
$R^1$ and $R^2$ are selected from the group consisting of hydrogen, methyl, ethyl, propyl, iso-propyl and butyl groups; and
$R_3$ selected from the group consisting of alkyl groups, alkenyl groups, and combinations thereof having from about 16 to about 22 carbon atoms.

23. A method for inhibiting fouling of equipment during solvent recovery in a diane plant producing a compound selected from the group consisting of 1,3-butadiene and isoprene, the method comprising treating a solvent recovery blend comprising extractive distillation solvent and at least one fouling agent with N,N-dimethyl amide of fatty acid in an amount and under conditions effective to inhibit said fouling.

24. The method of claim 23 further comprising separating said solvent from said blend.

25. The method of claim 24 wherein said solvent comprises acetonitrile.

26. A method for inhibiting fouling of equipment during solvent recovery in a diene plant producing a compound selected from the group consisting of
1,3-butadiene and isoprene, the method comprising:
treating a solvent recovery blend comprising extractive distillation solvent and at least one fouling agent with dispersant in an amount and under conditions effective to inhibit said fouling; and,
providing as said dispersant N,N-disubstituted amide having the following general formula:

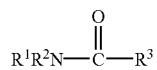

wherein:
$R_1$ and $R_2$ independently are selected from the group consisting of hydrogen atoms; hydroxyalkyl groups having from about 1 to about 3 carbon atoms; branched or unbranched alkyl groups and alkenyl groups having from about 1 to about 30 carbon atoms; and
$R_3$ is selected from the group consisting of hydrogen, aryl groups, alkaryl groups, alkaryl groups, and branched or unbranched alkyl groups and alkenyl groups having from about 1 to 30 carbon atoms.

27. The method of claim 26:
provided that,
when $R^1$ is selected from the group consisting of a hydrogen atom and alkenyl group, $R^2$ is $C_nH_{2n-z}$ wherein, when n is an even number, $R^1$ or $R^2$ has a quantity of carbon-carbon double bonds and said quantity increases from 1 to 2 to 3, to 4 to a maximum of n/2, with z following a first progression 1, 3, 5, 7, ... to n−1, depending of the number of alkene groups present; and when n is an odd number and said quantity increases from 1 to 2 to 3, to 4 to a maximum of (n−1)/2, with z following a second progression, 1, 3, 5, 7, ... to n−2.

28. The method of claim 27 wherein $R^1$ and $R^2$ independently are selected from the group consisting of hydrogen atoms; hydroxyalkyl groups having from about 1 to about 3 carbon atoms; branched or unbranched alkyl groups and alkenyl groups having from about 1 to about 6 carbon atoms.

29. The method of claim 27 wherein $R^1$ and $R^2$ independently are selected from the group consisting of alkyl groups having from about 1 to about 4 carbon atoms.

30. The method of claim 27 wherein $R^3$ is selected from the group consisting of branched and unbranched alkyl and alkenyl groups having from about 16 to 22 carbon atoms.

31. The method of claim 30 wherein $R^1$ and $R^2$ independently are selected from the group consisting of hydrogen atoms; hydroxyalkyl groups having from about 1 to about 3 carbon atoms; branched or unbranched alkyl groups and alkenyl groups having from about 1 to about 6 carbon atoms.

32. The method of claim 30 wherein $R^1$ and $R^2$ independently are selected from the group consisting of alkyl groups having from about 1 to about 4 carbon atoms.

33. The method of claim 26 wherein $R^3$ is selected from the group consisting of branched and unbranched alkyl and alkenyl groups having from about 16 to 22 carbon atoms.

34. The method of claim 33 wherein $R^1$ and $R^2$ independently are selected from the group consisting of hydrogen atoms; hydroxyalkyl groups having from about 1 to about 3 carbon atoms; branched or unbranched alkyl groups and alkenyl groups having from about 1 to about 6 carbon atoms.

35. The method of claim 33 wherein $R^1$ and $R^2$ independently are selected from the group consisting of alkyl groups having from about 1 to about 4 carbon atoms.

36. The method of claim 26 wherein $R^1$ and $R^2$ independently are selected from the group consisting of hydrogen atoms; hydroxyalkyl groups having from about 1 to about 3 carbon atoms; branched or unbranched alkyl groups and alkenyl groups having from about 1 to about 6 carbon atoms.

37. The method of claim 26 wherein $R^1$ and $R^2$ independently are selected from the group consisting of alkyl groups having from about 1 to about 4 carbon atoms.

* * * * *

UNITED STATES PATENT AND TRADEMARK OFFICE
CERTIFICATE OF CORRECTION

PATENT NO. : 7,182,839 B2
APPLICATION NO. : 09/923042
DATED : February 27, 2007
INVENTOR(S) : Marilyn Wood Blaschke It is certified that error appears in the above-identified patent and that said Letters Patent is hereby corrected as shown below:

On the Title Page, Item -56- OTHER PUBLICATIONS, delete "control" and insert -- Control --

Column 4, line 27 after "in" delete "a"

Column 9, line 27 delete "$R_1$ and $R_2$" and insert -- $R^1$ and $R^2$ --

Column 9, line 33 delete "$R_3$" and insert -- $R^3$ --

Column 9, line 62 delete "$R_3$" and insert -- $R^3$ --

Column 10, line 17 delete "wherein" and insert -- wherein: --

Column 10, line 21 delete "$R_3$" and insert -- $R^3$ is --

Column 10, line 25 delete "diane" and insert -- diene --

Column 10, line 53 delete "$R_1$ and $R_2$" and insert -- $R^1$ and $R^2$ --

Column 10, line 58 delete "$R_3$" and insert -- $R^3$ --

Column 10, line 59 delete "alkaryl" and insert -- aralkyl --

Signed and Sealed this

Twenty-second Day of May, 2007

JON W. DUDAS
*Director of the United States Patent and Trademark Office*